(12) United States Patent
Allard et al.

(10) Patent No.: US 7,601,179 B2
(45) Date of Patent: Oct. 13, 2009

(54) METHODS OF PRESERVING ARTIFICIAL COLORING ON KERATIN MATERIALS

(75) Inventors: Delphine Allard, Westfield, NJ (US); David W. Cannell, Plainfield, NJ (US); Michael S. DeGeorge, Middletown, NJ (US); Jeremy Puco, Budd Lake, NJ (US); Jonathan Wright, New Brunswick, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/855,598

(22) Filed: Sep. 14, 2007

(65) Prior Publication Data

US 2009/0074702 A1    Mar. 19, 2009

(51) Int. Cl.
*A61Q 5/10*    (2006.01)
(52) U.S. Cl. .................. 8/405; 8/407; 8/428; 8/552; 8/581; 132/202; 132/208

(58) Field of Classification Search ............... 8/405, 8/407, 428, 552, 581; 132/202, 208
See application file for complete search history.

(56) References Cited

U.S. PATENT DOCUMENTS

2005/0158260 A1 * 7/2005 Ferrari et al. .................. 424/63

FOREIGN PATENT DOCUMENTS

WO    WO 2005/060922 A1 *  7/2005

OTHER PUBLICATIONS

U.S. Appl. No. 11/855,450, filed Sep. 14, 2007, Allard, et al.

* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

The invention relates to methods of preserving artificial color on keratin materials including applying to artificially colored keratin materials a composition containing at least one silicone film forming resin and at least one polysilicone polymer.

8 Claims, No Drawings

METHODS OF PRESERVING ARTIFICIAL COLORING ON KERATIN MATERIALS

FIELD OF THE INVENTION

The present invention relates to methods of preserving artificial coloring on keratin materials comprising applying to an artificially colored keratin material a composition comprising at least one polysilicone polymer and at least one silicone resin. Such methods allow artificial colorant to remain on the keratin material for a substantial period of time.

DISCUSSION OF THE BACKGROUND

U.S. Pat. No. 5,800,816 discloses makeup compositions containing silicone resins, silicone oil and pigments which are reportedly transfer-resistant.

U.S. Pat. No. 6,074,654 discloses makeup compositions containing silicone resins, silicone gum and pigments which are reportedly transfer resistant.

However, this prior art does not disclose and/or enable methods of preserving artificial coloring on keratin materials, particularly methods in which a silicone film forming resin forms a film on the keratin material and the film fixes colorant to the keratin material, thereby resulting in artificial coloration which remains on the keratin material for a substantial amount of time (for example, artificial coloration which remains on hair, skin or lips through multiple washings or shampooings).

With specific reference to coloring hair, in the past, methods for artificially coloring hair using pigments and some dyes resulted in coloration which could be easily removed or which only last through a few washing cycles, or which fades after a certain number of washes. Thus, for example, past methods involving application of permanent dyes to hair have resulted in artificial coloring that fade after certain number of washings. Also, past methods have involved applications of "direct dyes", pigments, and semi-permanent dyes to hair which typically produce shorter-lived artificial coloring as compared to permanent dyes (that is, the artificial color fades in a shorter period of time).

Thus, a need exists for improved methods for preserving the artificial coloring of keratin materials (e.g., hair, skin, lips), particularly methods which result in artificial coloration which remains on the keratin material for a substantial or longer period of time and/or which provide the keratin material with pleasant texture and/or feeling upon touch.

Accordingly, one aspect of the present invention is a composition which is able to address or overcome at least some of the aforementioned problems associated with the prior art compositions, and allows the preservation of artificial coloring on keratin materials.

SUMMARY OF THE INVENTION

The present invention relates to methods for preserving artificial coloring on a keratin material comprising applying to a keratin material which has been artificially colored a composition comprising at least one silicone film forming resin and at least one polysilicone polymer. Preferably, when the composition is applied to the keratin material, the silicone film forming resin and the polysilicone polymer form a film on the keratin material and the film fixes the previously applied colorant to the keratin material.

The present invention also relates to methods for preserving highlighting on hair comprising applying to hair which has been highlighted a composition comprising at least one silicone film forming resin and at least one polysilicone polymer. Preferably, when the composition is applied to hair, the silicone film forming resin and the polysilicone polymer form a film on the hair and the film fixes the previously applied highlighting agent to the hair.

The present invention also relates to kits useful for applying artificial color to keratin materials and preserving artificial coloring on the keratin materials. The kits comprise a first composition comprising at least one colorant for imparting artificial colorant to a keratin material and a second composition comprising at least one silicone film forming resin and at least one polysilicone polymer, preferably a polysilicone copolymer. The kits may further comprise additional compositions such as, for example, a composition for removing artificial color from keratin materials, a composition for conditioning and/or moisturizing keratin materials, etc. Optionally, the kits may further comprise devices and/or instructions for artificially coloring keratin materials, preserving artificial color on keratin materials and/or removing artificial color from keratin materials.

It is to be understood that both the foregoing general description and the following detailed description are exemplary and explanatory only, and are not restrictive of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about".

As used herein, the expression "at least one" means one or more and thus includes individual components as well as mixtures/combinations.

"Cosmetically acceptable" means that the item in question is compatible with any keratin material. For example, "cosmetically acceptable medium" means a medium that is compatible with any keratin material.

"Keratin material" includes, for example, skin, hair, nails, eyelashes, eyelids, eyebrows, lips and any other area of body or facial skin.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing, paper or tissue or the skin. Transfer resistance may be evaluated by any method known in the art for evaluating such. For example, transfer resistance of a composition may be evaluated by application of the composition to a keratin material such as human hair, skin or lips followed by rubbing a material, for example, a sheet of paper, against the keratin material after expiration of a certain amount of time following application, such as 2 minutes after application. Similarly, transfer resistance of a composition may be evaluated by the amount of product transferred from a wearer to any other substrate, such as transfer from the keratin material of an individual to a collar when putting on clothing after the expiration of a certain amount of time following application of the composition to the keratin material. The amount of composition transferred to the substrate (e.g., collar, or paper) may then be evaluated and compared. For example, a composition may be transfer resistant if a majority of the product is left on the wearer's skin, hair or lips.

Further, the amount transferred may be compared with that transferred by other compositions, such as commercially available compositions. In a preferred embodiment of the present invention, little or no composition is transferred to the substrate from the keratin material.

"Preserve artificial coloring" as used herein refers to artificial coloring which has been applied to a keratin material remaining the same or substantially the same as at the time of application, as viewed by the naked eye, after an extended period of time. Thus, for example, a composition preserves artificial coloring if the color supplied to the keratin material remains the same or substantially the same for an extended period of time such as, for example, after two washings or shampooings, after 5 washings or shampooings, after 10 washings or shampooings, after 15 washings or shampooings, etc. Synonyms include, but are not limited to, fade resistance, impeding or inhibiting color intensity, fading and/or brightness, and the like. Color preservation properties may be evaluated by any method known in the art for evaluating such properties.

For example, artificial color preservation or fade resistance properties of the artificial color may be evaluated by a test involving the application of a composition to a keratin material and evaluating the color of the composition after an extended period of time. For example, the color provided to hair by an artificial hair coloring composition may be evaluated immediately following application to hair and these characteristics may then be re-evaluated at a later time (for example, after washing or shampooing or environmental stress) and compared to the initial evaluation.

Further, these characteristics may be evaluated with respect to other compositions, such as commercially available compositions. A sample protocol for such evaluation, using hair as an example of a keratin material, is as follows:

1. Swatches of Naturally White Hair (or 90% Grey Hair) are dyed with a hair color (for example, a direct dye).
2. Swatches are optionally treated with a fade-resistance treatment.
3. Swatches are paired (one treated, one untreated) and wetted, shampooed, rinsed and dried.
4. The process of step 3 is repeated until there is a noticeable difference.

Such a process can be repeated until there is an observable difference or lack thereof which usually requires 5-20 shampoos depending on the treatments and formulas. No difference after 20 shampoos is considered similar fading.

"Long wear" compositions as used herein, refers to compositions where at least one property chosen from consistency, texture, and color remains the same as at the time of application, as viewed by the naked eye, after an extended period of time, such as, for example, 1 week, 2 weeks, and further such as 1 month or 2 months. Long wear properties may be evaluated by any method known in the art for evaluating such properties. For example, long wear may be evaluated by a test involving the application of a composition to human hair and evaluating the consistency, texture and color of the composition after an extended period of time. For example, the consistency, texture and color of a hair composition may be evaluated immediately following application and these characteristics may then be re-evaluated and compared after an individual has worn the hair composition for a certain amount of time. Further, these characteristics may be evaluated with respect to other compositions, such as commercially available compositions.

"Waterproof" as used herein refers to the ability to repel water and permanence with respect to water. Waterproof properties may be evaluated by any method known in the art for evaluating such properties. For example, a hair composition may be applied to false hair or eyelashes, which may then be placed in water for a certain amount of time, such as, for example, 20 minutes. Upon expiration of the pre-ascertained amount of time, the false hair or eyelashes may be removed from the water and passed over a material, such as, for example, a sheet of paper. The extent of residue left on the material may then be evaluated and compared with other compositions, such as, for example, commercially available compositions. For example, a composition may be waterproof if a majority of the product is left on the wearer, e.g., eyelashes, hair, etc.

The cosmetic compositions, kits and methods of the present invention can comprise, consist of, or consist essentially of the essential elements and limitations of the invention described herein, as well as any additional or optional ingredients, components, or limitations described herein or otherwise useful in personal care compositions intended for topical application to keratin materials.

The composition of the present invention may be in any form. For example, it may be a paste, a solid, a gel, a lotion, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The composition can also be in a form chosen from a translucent anhydrous gel and a transparent anhydrous gel. The composition of the invention may, for example, comprise an external or continuous fatty phase. The composition may be anhydrous. The composition can also be a molded composition or cast as a stick or a dish. The composition in one embodiment is a solid such as a molded stick or a poured stick.

Stability of a composition is tested by placing the composition into simulated conditions, removing the composition at varied time intervals and physico-chemically testing the composition against other formulations or specifications. Simulated conditions can vary depending on expected storage conditions and formula susceptibilities. Examples of such conditions include various constant temperatures (both above and below room temperature), varied temperatures (freeze-thaw or heat-cool cycles), humidity storage, and exposure to sunlight. Samples can also observed for changes in appearance, odor or fragrance to determine composition stability.

First Composition Comprising Colorant

According to the present invention, compositions comprising at least one colorant are provided. Such first compositions, when applied to keratin material, artificially color the keratin material. Thus, such first compositions can be, for example, foundations, lipsticks, mascaras, hair dyes or any cosmetic composition which imparts color to a keratin material. This first composition can also be thought of as a "basecoat" because it is first applied to a keratin, and then the second composition is applied to the first composition. Accordingly, the second composition can also be thought of as a "topcoat."

Any suitable colorant can be used in accordance with the present invention as long as it provides artificial coloring to the keratin material to which it has been applied. One skilled in the art would readily be able to determine appropriate colorants for the keratin material sought to be colored. For example, dyes may be more appropriate for certain hair coloring applications, whereas pigments may be more appropriate for certain skin or lip coloring applications, as is known in the art.

Suitable colorants include, but are not limited to, pigments, liposoluble dyes, direct dyes, oxidation dyes, nacreous pigments, pearling agents, leuco dyes, optical lightening colorants, natural colorants and optically-variable pigments.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, DC Blue No. 14, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, silica, ferric blue, and mixtures thereof. Representative examples of organic pigments include carbon black, pigments of D & C type, and lakes based on cochineal carmine, barium, strontium, calcium, and aluminum. Other examples of pigments are ultramarines, HC Blue No. 14, Ext. Yellow 7, Yellow 10 Lake, and acid violet 43.

If present, the pigments may be present in the composition in a concentration ranging up to 50% by weight of the total weight of the composition, such as from 0.5% to 40%, and further such as from 2% to 30%.

A direct dye is a colored substance that does not require the use of an oxidizing agent in order to reveal its color. Suitable direct dyes which may be used according to the present invention may be chosen from acidic (anionic), basic (cationic), and neutral dyes.

"Acidic dye" is generally intended to mean a dye containing at least one COOH, $SO_3H$, $PO_3H$, or $PO_4H_2$ group, it being possible for said groups to exist in the form of salts. "Salts" is generally intended to mean salts of metals (for example, alkali metals or alkaline earth metals), salts of an organic amine that is optionally hydroxylated. Such dyes are also referred to as anionic dyes.

The acidic dyes that can be used in the context of this invention can be chosen from acidic nitro dyes, acidic azo dyes, acidic azine dyes, acidic triarylmethane dyes, acidic quinone dyes, acidic indo-amine dyes and acidic natural dyes, and mixtures thereof.

By way of illustration, mention may be made of the following dyes:

sodium salt of 2,4-dinitro-1-naphthol-7-sulphonic acid;
Acid Orange 3;
Acid Yellow 9/Food Yellow 2;
Direct Red 45/Food Red 13;
Acid Black 52;
Acid Yellow 36;
sodium salt of 1-hydroxy-2-(2',4'-xylyl-5-sulphonatoazo) naphthalene-4-sulphonic acid/Food Red 1;
Acid Red 14/Food Red 3/Mordant Blue 79;
Acid Red 18;
Acid Brown 4;
Acid Orange 7/Pigment Orange 17/Solvent Orange 49;
Food Yellow 3/Pigment Yellow 104;
Acid Red 27/Food Red 9;
Acid Orange 10/Food Orange 4;
Acid Red 44;
Acid Red 33/Food Red 12;
sodium salt of 1-(3'-nitro-5'-sulpho-6'-oxophenylazo)-8-acetamidonaphthalene-3,6-disulphonic acid/Food Red 11;
sodium salt of 1-hydroxy-2-(2'-methylphenylazo)-8-acetamidonaphthalene-3,6-disulphonic acid/Acid Red 35;
Acid Violet 3;
Acid Violet 43;
Acid Red 35;
Acid Violet 7;
Acid Red 135;
Acid Yellow 27;
Acid Yellow 23/Food Yellow 4;
Acid Yellow 36;
4'-(sulphonato-2",4"-dimethyl)bis-(2,6-phenylazo)-1,3-dihydroxybenzene/Acid Orange 24;
Acid Black 1 (sodium salt of 1-amino-2-(4'-nitrophenylazo)-7-phenylazo-8-hydroxynaphthalene-3,6-disulphonic acid);
(4-((4-methylphenyl)sulphonyloxy)phenylazo)2,2'-dimethyl-4-((2-hydroxy-5,-8-disulphonato)naphthylazo)biphenyl/Acid Red 111;
Food Black 2;
1-(4'-sulphonatophenylazo)-4-((2"-hydroxy-3"-acetylamino-6",8"-disulphonato)naphthylazo)-6-sulphonatonaphthalene (tetrasodium salt)/Food Black 1;
4-.beta.-hydroxyethylamino-3-nitro benzenesulphonic acid;
Acid Blue 9;
(5',6' or 7')-sulphonato-6'-methylquinoline-2,2',.DELTA.-1,3-indanedione/Acid Yellow 3;
sodium salt of 4-hydroxy-3((2-methoxyphenyl)-azo)-1-naphthalenesulphonic acid/Acid Red 4;
2-piperidino 5-nitrobenzenesulphonic acid;
2-(4'-N,N-(2"-hydroxyethyl)amino-2'-nitro) anilineethanesulphonic acid;
4-.beta.-hydroxyethylamino-3-nitrobenzenesulphonic acid;
Acid Violet 49; Acid Blue 7;
Acid Blue 156;
Acid Blue 317; and
Acid Blue 62.

Most of these dyes are described in particular in the Color Index published by The Society of Dyers and Colorists, P.O. Box 244, Perkin House, 82 Grattant Road, Bradford, Yorkshire, BD1 2JBN England, the entire contents of which is hereby incorporated by reference.

"Basic dyes" is generally intended to mean a dye that has at least one group bearing a positive charge, such as an ammonium group or a quaternized nitrogen atom in a ring. Such dyes are also referred to as cationic dyes.

The basic dyes that can be used in the context of this invention can be chosen from nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylamethane-derived dyes and basic natural dyes, and mixtures thereof.

Among the direct dyes that can be used according to the invention, mention may be made of the dyes described in Patent Applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369, FR 2 844 269, US 2007/0006398, US 2006/0130244, U.S. Pat. Nos. 7,179,301, 5,980,587, and 6,368,360, the entire contents of all of which are hereby incorporated by reference in their entirety.

Illustrative of such dyes are the following dyes:

1,3-dimethyl-2-[[4-(dimethylamino)phenyl]azo]-1H-imidazolium chloride;

1,3-dimethyl-2-[(4-aminophenyl)azo]-1H-imidazolium chloride;

1-methyl-4-[(methylphenylhydrazono)methyl]-pyridinium methyl sulphate;

Basic Red 22;
Basic Red 76;
Basic Yellow 57;
Basic Brown 16;
Basic Blue 41;
Basic Blue 67;
Basic Brown 1;
Basic Brown 4;
Basic Red 18;
Basic Red 46;
Basic Red 104;
Basic Red 118;
Basic Violet 35;
Basic Yellow 45;
Basic Yellow 67;
Basic Red 14;
Basic Yellow 13;
Basic Yellow 29;
Basic Brown 17;
Basic Blue 22;
Basic Blue 99;

1-N-methylmorpholiniumpropylamino-4-hydroxyanthraquinone;

Basic Blue 17;
Basic Red 2;
Basic Green 1;
Basic Violet 3;
Basic Violet 14;
Basic Blue 7; and
Basic Blue 26.

Preferably, the direct dyes may be present in amounts ranging from 0.001% to 30% by weight; from 0.01% to 20% by weight, from 0.1% to 10% by weight, including all ranges and subranges therebetween, with all weights being based on the total weight of the composition.

Representative oxidation dyes include those chosen from oxidation bases and oxidation couplers. Representative oxidation dyes include ortho- and para-phenylenediamines, double bases, ortho- and para-aminophenols and heterocyclic bases as well as their addition salts with an acid such as those described in U.S. patent application publication no. 2002/0013972, the entire contents of which is hereby incorporated by reference.

Among the para-phenylenediamines, mention may be made of para-phenylenediamine, 2-methyl-para-phenylenediamine, 1-(N-ethyl-N'-,β-hydroxyethyl)-amino-4-aminobenzene, 1-N,N'-bis(β-hydroxyethyl)amino-4-aminobenzene, 1-N,N'-bis(β,γ-dihydroxypropyl)amino-4-aminobenzene, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 4-amino-N,N-diethyl-2-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 4-amino-N-ethyl-N-carbamylmethylaniline, 4-amino-3-methyl-N-ethyl-N-carbamylmethylaniline, 4-amino-N-ethyl-N-(β-piperidinoethyl)aniline, 4-amino-3-methyl-N-ethyl-N-(β-piperidinoethyl)aniline, 4-amino-N-ethyl-N-(β-morpholinoethyl)aniline, 4-amino-3-methyl-N-ethyl-N-(β-morpholinoethyl)aniline, 4-amino-ethyl-N-(β-acetylaminoethyl)aniline, 4-amino-N-(β-methoxyethyl)aniline, 4-amino-β-methyl-N-ethyl-N-(β-acetylaminoethyl)aniline, 4-amino-N-ethyl-N-(β-mesylaminoethyl)aniline, 4-amino-3-methyl-N-ethyl-N-(β-mesylaminoethyl)aniline,4-amino-N-ethyl-N-(β-sulphoethyl)aniline, 4-amino-3-methyl-N-ethyl-N-(β-sulphoethyl)aniline, N-[4'-(amino)phenyl]morpholine, N[4'-(amino)phenyl]piperidine, N-(4'-aminophenyl)-para-phenylenediamine, N-phenyl-para-phenylenediamine, 2-fluoro-para-phenylenediamine, 2-carboxy-para-phenylenediamine, 2-sulpho-para-phenylenediamine, 2-isopropyl-para-phenylenediamine, N-(β hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, 2-β-hydroxyethyloxy-para-phenylenediamine, 2-β-acetylaminoethyloxy-para-phenylenediamine, N-β-methoxyethyl-para-phenylenediamine, para-toluylenediamine, 2-n-propyl-para-phenylenediamine, 1,β-methoxyethylamino-4-aminobenzene, 4-aminophenyl 1-(3-hydroxy)pyrrolidone, and acid addition salts thereof.

Among the ortho-phenylenediamines, mention may be made of 4-Methyl-o-Phenylenediamine, and acid addition salts thereof. As used herein, the term double bases means compounds comprising at least two aromatic nuclei having at least one of amino and hydroxyl groups.

Among the double bases that can be used as oxidation bases in the dye compositions disclosed herein, mention may be made of amino, mono($C_1$-$C_4$)alkylamino, di($C_1$-$C_4$)alkylamino, tri($C_1$-$C_4$) alkylamino, monohydroxy($C_1$-$C_4$)alkylamino, imidazolinium, and ammonium radicals. Mention may also be made of N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis-(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid addition salts thereof.

Among the para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Among the heterocyclic bases that can be used as oxidation bases in the dye compositions in accordance with certain embodiments, mention may be made of pyridine derivatives, pyrimidine derivatives, pyrazole derivatives, pyrazolinone derivatives, and the acid addition salts thereof.

Among the pyridine derivatives, mention may be made of the compounds described, for example, in patents GB 1,026, 978 and GB 1,153,196, as well as the compounds 2,5-diaminopyridine, 2-(4-methoxyphenyl)amino-3-aminopyridine, 2,3-diamino-6-methoxypyridine, 2-(β-methoxyethyl)amino-3-amino-6 methoxypyridine, 3,4-diaminopyridine, and the acid addition salts thereof.

Among the pyrazole and pyrazolinone derivatives, mention may be made the compounds described in patents DE 3,843,892, DE 4,133,957 and patent applications WO 94/08969, WO 94/08970, FR-A-2,733,749, and DE 195 43 988, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1, 3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, 2-(4,5-diamino-1H-pyrazol-1-yl), and the acid addition salts thereof.

The oxidation bases, if present, may be employed in amounts ranging from 0.0001% to 12% by weight; from 0.001% to 8% by weight, all weights being based on the total weight of the composition.

Representative couplers include those conventionally used in oxidation dye compositions, that is to say meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and the acid addition salts thereof.

These couplers may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1, 2,4-triazole, 2,6-dimethylpyrazolo[1,5-b]-1,2,4-triazole, 6-methyl pyrazolo [1,5-a]-benzimidazole, and the acid addition salts thereof.

When they are present, these couplers may be present in amounts ranging from 0.0001% to 12% by weight; from 0.001% to 8% by weight, all weights being based on the total weight of the composition.

In general, the acid addition salts of the oxidation bases and couplers may be chosen from hydrochlorides, hydrobromides, sulphates, tartrates, lactates, and acetates.

Representative leuco dyes include those disclosed in US patent application publication no. 20040194231, the entire contents of which is hereby incorporated by reference. Leuco dyes are usually only slightly colored or are not colored at all and can be converted by simple oxidation in air or in the presence of an oxidizing agent into a triheteroylmethane compound. Examples of leuco dyes and corresponding triheteroylmethane compounds include 1H-Benzo[ij]quinolizinium, 9-[bis(2,3,6,7-tetrahydro-1H ,5H-benzo[ij-]quinolizin-9-yl)methylene]-2,3,5,6,7,9-hexahydro-chloride; 5H-Benzo[a]carbazolium, 11-ethyl-5-[(11-ethyl-11H-benzo[a]carbazol-5-yl)(1-ethyl-1,2,3,4-tetrahydro-5-quinolinyl) methylene]-; Pyrrolo[3,2,1-ij]quinolinium, 8-[bis(1,2,5,6-tetrahydro-4H-pyrrolo[-3,2,1-ij]quinolin-8-yl)methylene]-1, 2,4,5,6,8-hexahydro-; Tri(9-ethy-9H-carbazol-3-yl) methane; Bis(6-Chloro-9-ethy-9H-carbazol-3-yl)-(9-ethy-9H-carbazol-3-yl)methane; Bis(1-(4-sulfo-butyl)-2,3,4,6-tetrahydro-quinolinium)-pyrid-4-yl-methane; Bis(1-ethyl-2-methyl-1H-indol-3-yl)-(9-ethy-9H-carbazol-3-yl)methane; Tri(7-ethyl-7H-benzo[c]carbazol-10-yl)methane; Bis((6-dimethylamino-3-methyl-1H-indol-2-yl)-2-furylmethane; Bis((6-dimethylamino-3-methyl-1H-indol-2-yl)-(pyrid-4-yl)methane; Bis(1-ethyl-2-methyl-1H-indol-3-yl)-2-thienylmethane; 3-[(1-ethyl-2-methyl-1H-indol-3-yl)-(9-ethy-9H-carbazol-3-yl)methylene]-1-ethyl-2-methyl-3H-indolium; and 3-[(1-ethyl-2-methyl-1H-indol-3-yl)-2-thienyl)methylene]-1-ethyl-2-methyl-3H-indolium.

Representative optical lightening colorants include those disclosed in US patent application publication no. US20040205905, the entire contents of which is hereby incorporated by reference.

Representative natural colorants include those disclosed in US patent application publication no. US20030159221, the entire contents of which is hereby incorporated by reference. For the purposes of the invention, the expression "natural colorant" means compounds that exist in nature, whether they have been obtained by extraction or reproduced chemically. Examples of natural direct dyes that may be used according to the invention include lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes and especially henna-based poultices or extracts.

Second Composition

Silicone Film Forming Resin

According to the present invention, second compositions comprising at least one silicone film forming resin are provided.

Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares one oxygen when the unit is part of a polymer. The "M" unit can be represented by the following structure:

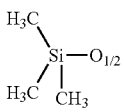

At least one of the methyl groups of the M unit may be replaced by another group, e.g., to give a unit with formula [R(CH$_3$)$_2$]SiO$_{1/2}$, as represented in the following structure:

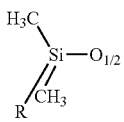

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, aryl groups and phenyl groups, wherein the groups other than methyl groups may be not further substituted.

The symbol D denotes the difunctional unit (CH$_3$)$_2$SiO$_{2/2}$ wherein two oxygen atoms bonded to the silicone atom are used for binding to the rest of the polymer. The "D" unit, which is the major building block of dimethicone oils, can be represented as:

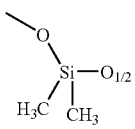

At least one of the methyl groups of the D unit may be replaced by another group, e.g., to give a unit with formula [R(CH$_3$)$_2$]SiO$_{1/2}$.

The symbol T denotes the trifunctional unit, (CH$_3$)SiO$_{3/2}$ and can be represented as:

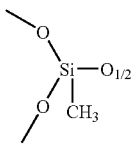

At least one of the methyl groups of the T unit may be replaced by another group, e.g., to give a unit with formula [R(CH$_3$)$_2$]SiO$_{1/2}$.

Similarly, the symbol Q denotes the tetrafunctional unit, SiO$_{4/2}$ wherein all four oxygens bonded to the silicone atom are bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

Non-limiting examples of silicone polymers include silanes, siloxanes, siloxysilicates, and silsesquioxanes. A non-limiting example of such a siloxane is polydimethylsiloxane (PDMS). Polydimethylsiloxanes are generally composed of long straight chains of (CH$_3$)$_2$SiO$_{2/2}$ (i.e., D units) and have viscosities which are dependent on both the size of the polymer and the presence and nature of any substituent(s) on the polymer. A non-limiting example of a siloxysilicate is trimethylsiloxysilicate, which may be represented by the following formula:

$$[(CH_3)_3-Si-O]_x-(SiO_{4/2})_y$$

(i.e, MQ units) wherein x and y may, for example, range from 50 to 80. Silsesquioxanes, on the other hand, may be represented by the following formula:

$$(CH_3SiO_{3/2})_x$$

(i.e., T Units) wherein x may, for example, have a value of up to several thousand.

Polymethylsilsesquioxanes are silsesquioxanes that do not have a substituent replacing the methyl groups. Certain polymethylsilsesquioxanes have previously been used in hair care compositions. See, e.g., U.S. Pat. No. 5,246,694, the disclosure of which is incorporated herein by reference, which discloses a shampoo composition comprising a surfactant, an aqueous emulsion of highly viscous silicone in volatile silicone and a cationic polymer which is a derivative of guar gum. The highly viscous silicone disclosed therein may be chosen from silicone resins including a polymethylsilsesquioxane such as Resin MK (also called SiliconHarz MK) which is available from Wacker, and a siloxysilicate such as Resin MQ which is available from General Electric and Dow Corning.

The Resin MK and Resin MQ silicone resins may form a film after a volatile carrier has evaporated. The MQ film is generally hard and brittle at room temperature, while the MK film is generally continuous and flexible, i.e., not brittle. Depending on the application, plasticizers may be added to help obtain a more flexible, thus more comfortable, film.

In one embodiment, the silicone film former may be a polymethylsilsesquioxane film former such as Belsil PMS MK, also referred to as Resin MK, available from Wacker Chemie. This polymethylsilsesquioxane film former is a polymer comprising polymerized repeating units of CH$_3$SiO$_{3/2}$ (T units) and may also contain up to 1% by weight or by mole of units of the formula (CH$_3$)$_2$SiO$_{2/2}$ (D units). The weight-average molecular weight of this polymer has been estimated to be 10,000. It is believed that the polymers are in a "cage" and "ladder" configuration, as exemplified in the figures below. The majority of the polymer is in the "ladder" configuration, wherein the ends of the polymer are capped with ethoxy (CH$_3$CH$_2$O) groups. The ethoxy groups are generally present in an amount of 4.5% by weight and the mole percent is generally 7% (silicone units). As ethoxy groups may react with water, a small and variable amount of SiOH may also be present in the polymer.

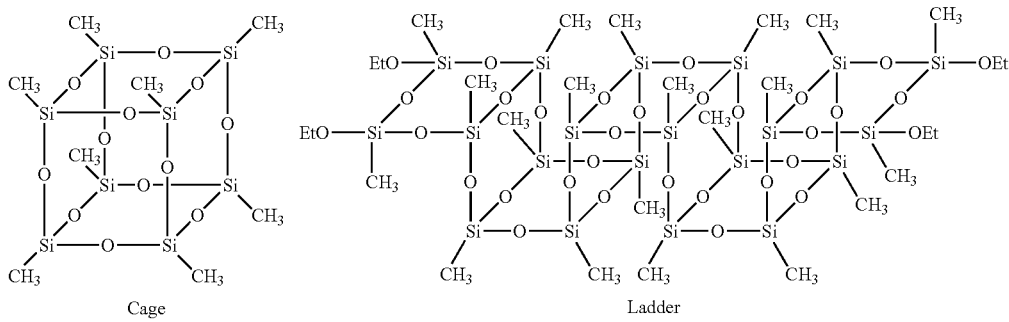

Cage    Ladder

Another non-limiting example of the at least one polymethylsilsesquioxane film former suitable for use in the present invention is KR-220L, which is available from SHIN-ETSU. This polymethylsilsesquioxane film former is composed of silicone T-units (i.e., those of formula $CH_3SiO_{3/2}$) and has Si—OH (or silanol) end units. There are no D units in KR-220L.

Other non-limiting examples of the at least one polymethylsilsesquioxane film former that may be useful in the practice of the invention include KR-242A (which is comprised of methyl T units (98%) and dimethyl D units (2%) and has Si—OH end units) and KR-251 (which is comprised of methyl T units (88%) and dimethyl D units (12%) and has Si—OH end units), both of which are available from SHIN-ETSU.

Depending on the application, the concentration of the at least one polymethylsilsesquioxane film former in the presently claimed composition may vary considerably. One of skill in the art will be able to determine routinely the amount of the at least one polymethylsilsesquioxane film former depending on the desired application.

In another embodiment, the silicone film former may be chosen from siloxysilicates. Preferably, the siloxysilicate is trimethylsiloxysilicate, which may or may not be in powder form. Trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Preferably, the at least one silicone resin film forming agent is present in an amount ranging from about 0.5% to about 60% by weight of the total weight of the composition, more preferably from about 1% to about 50% of the total weight of the composition, more preferably from about 2% to about 40% of the total weight of the composition, and most preferably from about 3% to about 25%, including all ranges and subranges therebetween.

Polysilicone Polymer

According to the present invention, second compositions comprising at least one polysilicone polymer are provided. Particularly preferred polysilicone polymers include, polysiloxane liquids, polysiloxane gums, polysiloxane waxes and polysiloxane containing thickening agents.

Suitable polysiloxane liquids include, but are not limited to, non-volatile linear polydimethylsiloxanes (PDMSs), polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, amodimethicone, bisphenylhexamethicone, dimethicone copolyol, dimethiconol, hexadecyl methicone, hexamethyldisiloxane, methicone, simethicone, dimethylhydrogensiloxane, vinyidimethicone, diphenyl methyldiphenyl trisiloxanes, and mixtures thereof.

For example, the liquid polysiloxane polymers may comprise repeating units, wherein said units correspond to the formula $(R_2SiO)$, where R is a monovalent hydrocarbon radical containing from 1 to 6 carbon atoms, preferably selected from the group consisting of methyl, ethyl, propyl, isopropyl, butyl, isobutyl, t-butyl, amyl, hexyl, vinyl, allyl, cyclohexyl, phenyl, fluoroalkyl and mixtures thereof, and may be terminated by triorganosilyl groups of the formula $(R'_3Si)$ where R' is a radical selected from the group consisting of monovalent hydrocarbons containing from 1-6 carbon atoms, hydroxyl groups, alkoxyl groups and mixtures thereof.

The polysiloxane liquids typically have a viscosity ranging from 200 to about 450,000 centipoise at 25° C., preferably 350 to 100,000 centipoise at 25° C.

Suitable polysiloxane gums include, but are not limited to, the same polysiloxane compounds discussed above in connection with polysiloxane liquids. However, the polysiloxane gums have greater viscosity than the liquids: that is, greater than 500,000 centipoise at 25° C., preferably greater than 750,000 centipoise at 25° C., preferably greater than 1,000,000 centipoise at 25° C., preferably greater than 2,000,000 centipoise at 25° C., and preferably greater than 5,000,000 centipoise at 25° C.

Polysiloxane gums can be found in commercially available products such as in mixture with a cyclic silicone oil, such as the product SF1214 from General Electric (which is a mixture of dimethicone gum, having a molecular weight of 500,000, dissolved in decamethylcyclopentasiloxane), or in mixture with a polysiloxane liquid such as, for example, the mixtures of two PDMSs with different viscosities, such as the product SF1236 from the company General Electric (which is a mixture of 15% of dimethicone gum having a molecular weight of 500,000, and of 85% of SF96 oil).

Suitable polysiloxane waxes include, but are not limited to, derivatives of the liquid polysiloxane polymers discusses above which have been derivatized through addition of at least one "fatty" carbon chain having at least 6 carbon atoms, preferably 7-50 carbon atoms, more preferably 12-45 carbon atoms and most preferably 14-28 carbon atoms. Such compounds are waxy solids or semi-solids at 25° C. Suitable examples include $C_{14-45}$ alkyl dimethicones such as cetyl dimethicone, C24/28 alkyl dimethicone wax, cetyl methicone, stearyl methicone, cetyl dimethicone, stearyl dimethicone, cerotyl dimethicone, C30-45 Alkyl Dimethicone and C30-45 Alkyl Methicone.

Suitable polysiloxane containing thickening agents include, but are not limited to, those chosen from homopolymers and copolymers, preferably, with a weight-average molecular mass ranging from about 500 to about $2.5 \times 10^6$ or more, comprising at least one moiety comprising: at least one polyorganosiloxane group comprising, preferably, from 1 to about 10,000 organosiloxane units in the chain of the moiety or in the form of a graft, and at least two groups capable of establishing hydrogen interactions are provided.

According to preferred embodiments of the present invention, the polysiloxane containing thickening agents used in the composition of the invention may belong to the following two families:
 a) polyorganosiloxanes comprising at least two groups capable of establishing hydrogen interactions, these two groups being located in the polymer chain; and/or
 b) polyorganosiloxanes comprising at least two groups capable of establishing hydrogen interactions, these two groups being located on grafts or branches.

The polysiloxane containing thickening agents of the present invention can be liquid or solid at room temperature. Preferably, the polymers are solid. When the polymers are solid, it is preferable that they can be dissolved before or during use in a solvent with hydrogen interaction capable of breaking the hydrogen interactions of the polymers, for instance $C_2$ to $C_8$ lower alcohols and especially ethanol, n-propanol or isopropanol. It is also possible to use these hydrogen interaction "breaking" solvents as co-solvents in the compositions of the present invention. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

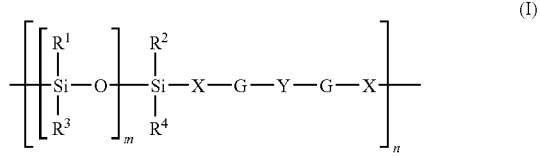

(I)

in which:
 1) $R^1$, $R^2$, $R^3$ and $R^4$, which may be identical or different, represent a group chosen from:
 linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms,
 $C_6$ to $C_{10}$ aryl groups, optionally substituted with one or more $C_1$ to $C_4$ alkyl groups,
 polyorganosiloxane chains possibly containing one or more oxygen, sulphur and/or nitrogen atoms;
 2) the groups X, which may be identical or different, represent a linear or branched $C_1$ to $C_{30}$ alkylenediyl group, possibly containing in its chain one or more oxygen and/or nitrogen atoms;
 3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
 4) Y represents a group corresponding to the formula:

in which
 T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
 $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may be linked to another chain of the polymer;
 5) the groups G, which may be identical or different, represent divalent groups chosen from:

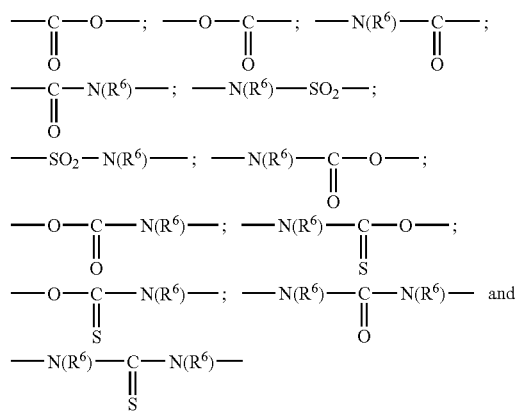

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

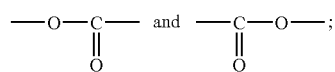

6) n is an integer of at least 1, for example ranging from 2 to 500 and preferably from 2 to 200, and m is an integer of at least one, ranging from 1 to 35,000, for example, from 1 to 10,000 and 1 to 2,500, from 1 to 700 and from 6 to 200, including all values and subranges there between.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups,
b) $C_{30}$ to $C_{56}$ branched alkylene groups possibly comprising rings and unconjugated unsaturations,
c) $C_5$-$C_6$ cycloalkylene groups,
d) phenylene groups optionally substituted with one or more $C_1$ to $C_{40}$ alkyl groups,
e) $C_1$ to $C_{20}$ alkylene groups comprising from 1 to 5 amide groups,
f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups,
g) polyorganosiloxane chains of formula:

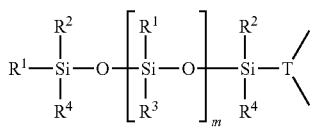

in which $R^1$, $R^2$, $R^3$, $R^4$, T and m are as defined above, and
h) polyorganosiloxane chains of formula:

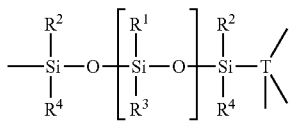

The polyorganosiloxanes of the second family may be polymers comprising at least one moiety corresponding to formula (II):

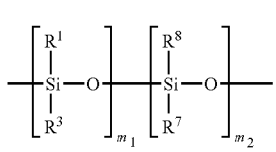

(II)

in which
$R^1$ and $R^3$, which may be identical or different, are as defined above for formula (I),
$R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above,
$m_1$ is an integer of at least one ranging from 1 to 35,000, for example, from 1 to 10,000 and 1 to 2,500, from 1 to 700, and from 6 to 200, including all values and subranges there between; and
$m_2$ is an integer of at least one ranging from 1 to 35,000, for example, from 1 to 10,000 and 1 to 2,500, from 1 to 700, and from 6 to 200, including all values and subranges there between.

According to the invention, the polysiloxane containing thickening agent may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to preferred embodiments, it is also possible to use a copolymer comprising at least one hydrocarbon-based moiety comprising two groups capable of establishing hydrogen interactions, chosen from ester, amide, sulphonamide, carbamate, thiocarbamate, urea and thiourea groups, and combinations thereof.

These copolymers may be block copolymers or grafted copolymers.

According to a first embodiment of the invention, the groups capable of establishing hydrogen interactions are amide groups of formulae —C(O)NH— and —HN—C(O)—. In a particularly preferred embodiment, the polyorganosiloxane containing polymer is a polysiloxane polyamide copolymer such as those described in U.S. patent application publication no.2004/0170586, the entire contents of which is hereby incorporated by reference.

In this case, the polymer may comprise at least one moiety of formula (III) or (IV):

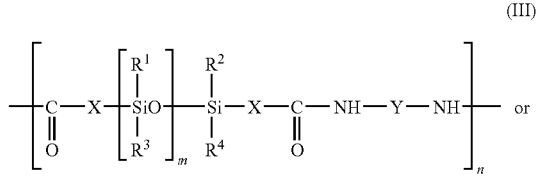

(III)

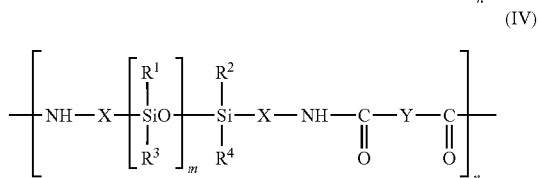

(IV)

in which $R^1$, $R^2$, $R^3$, $R^4$, X, Y, m and n are as defined above.
Such a moiety may be obtained:
either by a condensation reaction between a silicone containing α,ω-carboxylic acid ends and one or more diamines, according to the following reaction scheme:

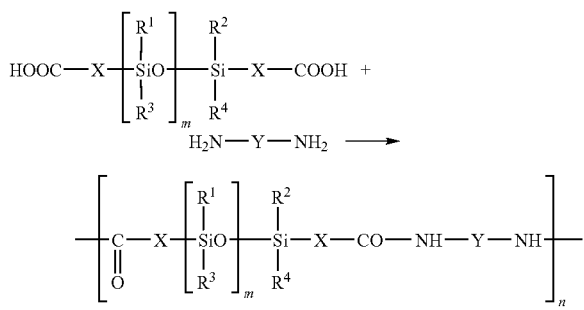

or by reaction of two molecules of α-unsaturated carboxylic acid with a diamine according to the following reaction scheme:

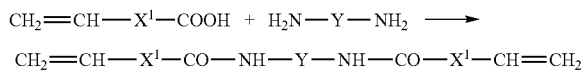

followed by the addition of a siloxane to the ethylenic unsaturations, according to the following scheme:

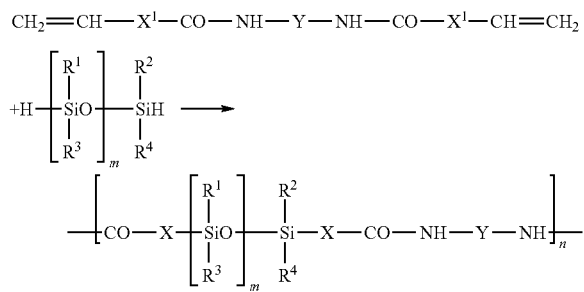

in which $X^1$—$(CH_2)_2$— corresponds to X defined above and Y, $R^1$, $R^2$, $R^3$, $R^4$ and m are as defined above;

or by reaction of a silicone containing α,ω-$NH_2$ ends and a diacid of formula HOOC—Y—COOH according to the following reaction scheme:

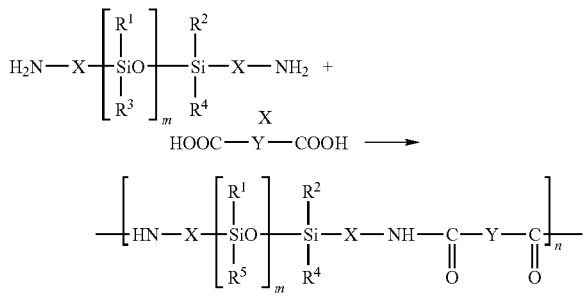

In these polyamides of formula (III) or (IV), m is an integer of at least one as defined above, and preferably in the range from 1 to 700, for example, from 15 to 500 and from 15 to 45, including all values and subranges there between; and n is in particular in the range from 1 to 500, for example, from 1 to 100 and from 4 to 25, including all values and subranges there between; X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, including from 1 to 20 carbon atoms and from 2 to 6 carbon atoms, including all values and subranges there between, for example, 6 carbon atoms.

In formulae (III) and (IV), the alkylene group representing X or Y can optionally contain in its alkylene portion at least one of the following elements:

1) 1 to 5 amide, urea or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^5$ represents a polyorganosiloxane chain and T represents a group of formula:

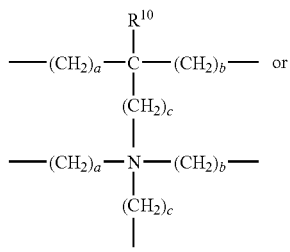

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

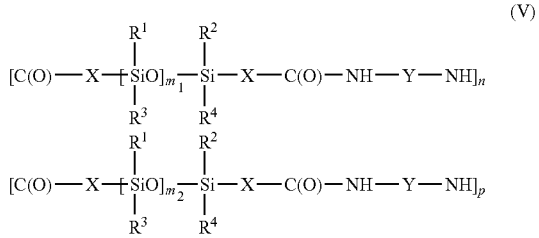
(V)

in which X, Y, n and $R^1$ to $R^4$ have the meanings given above, $m_1$ and $m_2$, which are different, are as defined above, and preferably are chosen in the range from 1 to 1000, and p is at least one for example ranging from 2 to 500 and preferably from 2 to 200.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

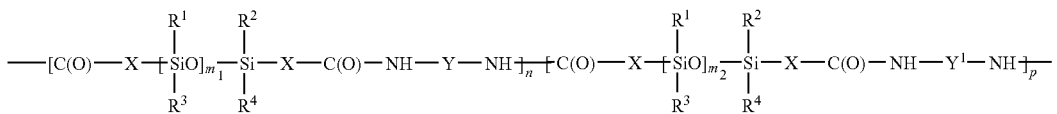
(VI)

in which $R^1$ to $R^4$, X, Y, $m_1$, $m_2$, n and p have the meanings given above and $Y^1$ is different from Y but chosen from the groups defined for Y. As previously discussed, the various moieties may be structured to form either a block copolymer, or a random copolymer or an alternating copolymer.

In an embodiment of the invention, the polysiloxane containing thickening agent may also contain a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

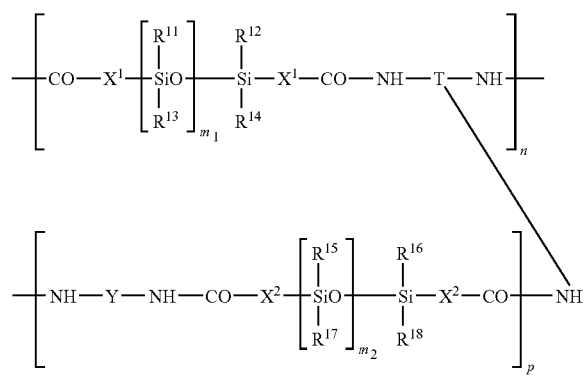
(VII)

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1,000, and p is an integer of at least one, for example, p can range from 2 to 500.

In formula (VII), it is preferred that:

p is in the range from 1 to 25, including from 1 to 7, including all values and subranges there between, $R^{11}$ to $R^{18}$ are methyl groups, T corresponds to one of the following formulae:

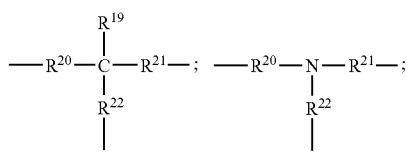

-continued

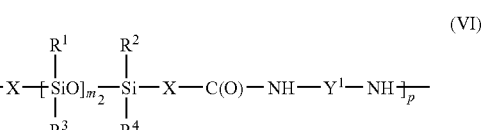

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

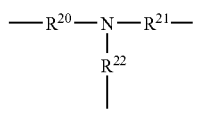

in particular with $R^{20}$, $R^{21}$ and $R^{22}$ representing —$CH_2$—$CH_2$—, $m_1$ and $m_2$ are in the range from 15 to 500, including from 15 to 45 and including all values and subranges there between, $X^1$ and $X^2$ represent —$(CH_2)_{10}$—, and Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:

polyamides of formula (III) in which m is from 15 to 300, for example, 15 to 100, including all values and subranges there between;

mixtures of two or more polyamides in which at least one polyamide has a value of m in the range from 15 to 50, including all values and subranges there between and at least one polyamide has a value of m in the range from 30 to 300, including all values and subranges there between;

polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;

mixtures of polyamide of formula (III) combining
1) 80% to 99% by weight of a polyamide in which n is equal to 2 to 10 and in particular 3 to 6, and
2) 1% to 20% of a polyamide in which n is in the range from 5 to 500 and in particular from 6 to 100;

polyamides corresponding to formula (VI) in which at least one of the groups Y and $Y^1$ contains at least one hydroxyl substituent;

polyamides of formula (III) synthesized with at least one portion of an activated diacid (diacid chloride, dianhydride or diester) instead of the diacid;

polyamides of formula (III) in which X represents —$(CH_2)_3$— or —$(CH_2)_{10}$; and polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:

a $C_1$ to $C_{50}$ alkyl ester group by introducing a $C_1$ to $C_{50}$ monoalcohol during the synthesis, a $C_1$ to $C_{50}$ alkylamide group by taking as stopping group a monoacid if the silicone is α,ω-diaminated, or a monoamine if the silicone is an α,ω-dicarboxylic acid.

According to one embodiment of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based polymers containing silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and for example, 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a gelling agent based on a copolymer between a hydrocarbon-based polyamide and a silicone polyamide, by transamidation of a polyamide having, for example, an ethylene-diamine constituent, with an oligosiloxane-α,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:

by hydrosilylation of unsaturated bonds in polyamides based on fatty acid dimers;

by silylation of the amide groups of a polyamide; or by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

The polysiloxane containing thickening agents used in the composition of the invention are most preferably polymers of the polyorganosiloxane type such as those described in documents U.S. Pat. No. 5,874,069, U.S. Pat. No. 5,919,441, U.S. Pat. No. 6,051,216 and U.S. Pat. No. 5,981,680, the entire disclosures of which are hereby incorporated by reference.

According to another embodiment of the invention, the polysiloxane containing thickening agent is a homopolymer or a copolymer comprising urethane or urea groups.

As previously discussed, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

$$\left[\left[\begin{array}{c} R^1 \\ | \\ Si-O \\ | \\ R^3 \end{array}\right]_m \begin{array}{c} R^2 \\ | \\ Si-X-U-C-NH-Y-NH-C-U-X \\ | \quad\quad\quad\quad \| \quad\quad\quad\quad\quad\quad \| \\ R^4 \quad\quad\quad\quad O \quad\quad\quad\quad\quad\quad O \end{array}\right]_n \quad (VIII)$$

in which $R^1$, $R^2$, $R^3$, $R^4$, X, Y, m and n have the meanings given above for formula (I), and U represents —O— or —NH—, such that:

$$-U-\underset{\underset{O}{\|}}{C}-NH-$$

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

$$-\!\!-\!\!\left[B^1-NH-\underset{\underset{O}{\|}}{C}-U-B^2-U-\underset{\underset{O}{\|}}{C}-NH\right]_d\!\!-\!\!B^1 \quad (IX)$$

in which $B^1$ is a group chosen from the groups given above for Y, U is —O— or —NH— and $B^2$ is chosen from:
  linear or branched $C_1$ to $C_{40}$ alkylene groups, which can optionally bear an ionizable group such as a carboxylic acid or sulphonic acid group, or a neutralizable or quaternizable tertiary amine group,
  $C_5$ to $C_{12}$ cycloalkylene groups, optionally bearing alkyl substituents, for example one to three methyl or ethyl groups, or alkylene, for example the diol radical: cyclohexanedimethanol,
  phenylene groups that may optionally bear $C_1$ to $C_3$ alkyl substituents, and groups of formula:

$$R^5-T\!\!\begin{array}{c}\diagup\\ \diagdown\end{array}$$

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

$$-(CH_2)_w-\underset{|}{CH}-CH_2- \quad \text{or}$$

$$-(CH_2)_w-O-\underset{|}{CH}-CH_2-$$

with w being an integer ranging from 1 to 10 and $R^5$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —$(CH_2)_2$— or —$(CH_2)_6$— or a group:

$$\begin{array}{c}\diagdown\\ T-R^5\\ \diagup\end{array}$$

with $R^5$ being a polyorganosiloxane chain.

As previously discussed, the polysiloxane containing thickening agent may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

$$\left[\begin{array}{c} R^1 \\ | \\ Si-O \\ | \\ R^3 \end{array}\right]_{m_1} \left[\begin{array}{c} R^2 \\ | \\ Si-O \\ | \\ R^{23} \\ | \\ CH_2 \\ | \\ U \\ | \\ O=C-NH-R^{24} \end{array}\right]_{m_2} \quad (X)$$

in which $R^1$, $R^2$, $R^3$, $m_1$ and $m_2$ have the meanings given above for formula (I),
  U represents O or NH,
  $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used, for example, as gelling agents in the compositions of the invention The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

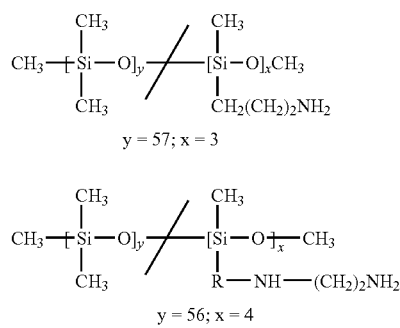

In these formulae, the symbol "/" indicates that the segments may be of different lengths and in a random order, and R represents a linear aliphatic group preferably containing 1 to 6 carbon atoms, including 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

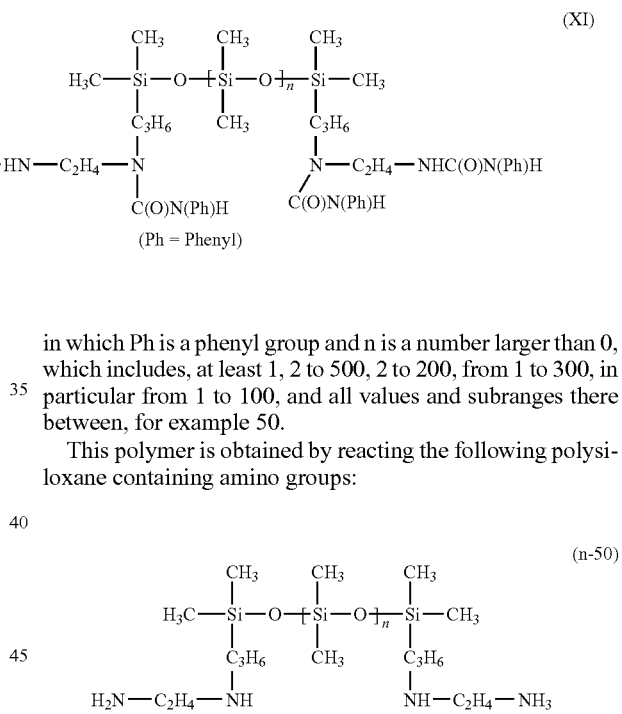

in which Ph is a phenyl group and n is a number larger than 0, which includes, at least 1, 2 to 500, 2 to 200, from 1 to 300, in particular from 1 to 100, and all values and subranges there between, for example 50.

This polymer is obtained by reacting the following polysiloxane containing amino groups:

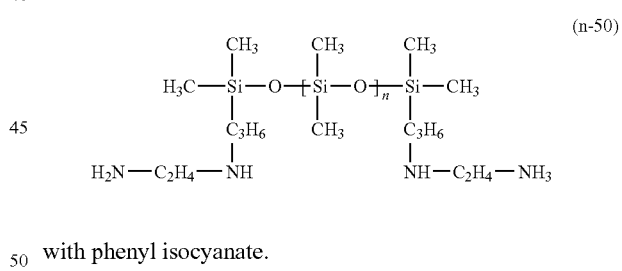

with phenyl isocyanate.

The polymers of formula (VIII) comprising urea or urethane groups in the chain of the silicone polymer may be obtained by reaction between a silicone containing $\alpha,\omega$-$NH_2$ or —OH end groups, of formula:

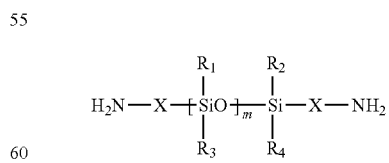

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

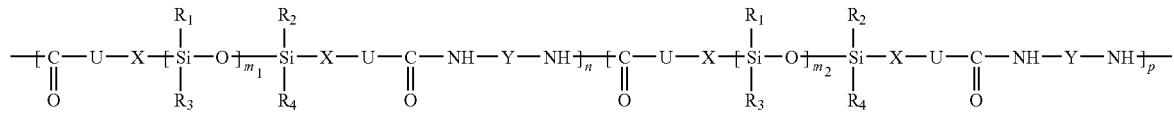

(XII)

in which $R^1, R^2, R^3, R^4, X, Y$ and U are as defined for formula (VIII) and $m_1, m_2$, n and p are as defined for formula (V).

Branched polyurethane or polyurea silicones may also be obtained using, instead of the diisocyanate OCN—Y—NCO, a triisocyanate of formula:

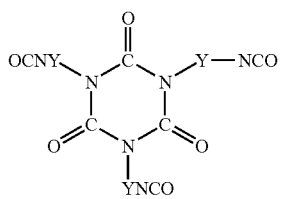

A polyurethane or polyurea silicone containing branches comprising an organosiloxane chain with groups capable of establishing hydrogen interactions is thus obtained. Such a polymer comprises, for example, a moiety corresponding to the formula:

(XIII)

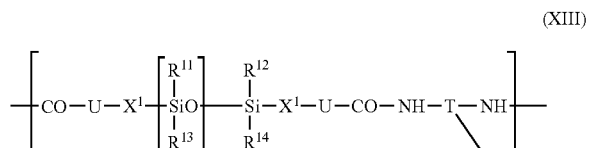

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are as defined above.

As in the case of the polyamides, this copolymer can also comprise polyurethane silicone moieties without branching.

In another embodiment of the invention, the siloxane-based polyureas and polyurethanes that are preferred are:

polymers of formula (VIII) in which m is from 15 to 300, for example, 15 to 100 and all values and subranges there between;

mixtures of two or more polymers in which at least one polymer has a value of m in the range from 15 to 50 and at least one polymer has a value of m in the range from 30 to 300, including all values and subranges there between;

polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;

mixtures of polymer of formula (Vil) combining
1) 80% to 99% by weight of a polymer in which n is equal to 2 to 10 and in particular 3 to 6, and
2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

(1)

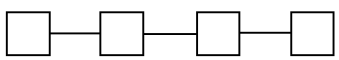

(2)

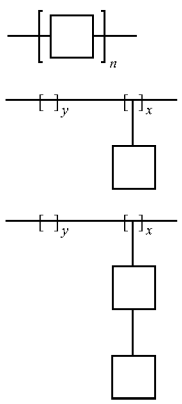

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. Preferably, the values n, x and y are such that the polymer has the desired properties in terms of an agent for gelling fatty phases, preferably fatty phases based on silicone oil.

As examples of polymers that may be used, mention may be made of the silicone polyamides obtained in accordance with the disclosure in U.S. Pat. No. 5,981,680, the entire disclosure of which is hereby incorporated by reference.

Further examples of polysiloxane containing thickening agents are set forth in U.S. Pat. Nos. 6,503,632 and 6,569,955, both of which are hereby incorporated by reference in their entirety.

As noted above, the polysiloxane containing thickening agents of the present invention can be solid or liquid at room temperature. When solid, the polymers preferably have a softening point from 50 to 130° C. Most preferably, they have a softening point ranging from 65 to 150° C., including from 70° C. to 130° C. This softening point is lower than that of other structuring polymers, which facilitates the use of the polymers that are the subject of the invention, and limits the deteriorations of the liquid fatty phase.

As noted above, the polysiloxane containing thickening agents of the present invention contain both siloxane units and at least two groups capable of establishing hydrogen interactions such as amide linkages. The siloxane units can provide compatibility with a silicone fluid, if present, (for example with the cyclomethicones), while the groups capable of establishing hydrogen interactions and the spacing and selection of the locations of the amide linkages can facilitate gelation and the formation of cosmetic products.

In one embodiment, the polysiloxane containing thickening agent of the present invention is present in an amount effective to provide transfer resistant properties, and may also provide at least one of the following properties: pliability, softness, and wearing comfort. In addition, it is preferred that the compositions of the invention exhibit flexibility and/or good adherence on the hair to which the compositions have been applied. In another preferred embodiment, the compositions of the present invention when applied to the hair are substantially non-tacky.

In the compositions of the present invention, the polysilicone polymers are preferably present in an amount of 0.1-80 percent by weight, more preferably from 0.5 to 30 percent by weight and most preferably from 1 to 20 percent by weight of the total weight of the composition, including all ranges and subranges therebetween.

According to particularly preferred embodiments of the present invention, the ratio of silicone resin to polysilicone polymer present in the composition, by weight, ranges from about 1:1 to about 10:1, more preferably from about 2:1 to about 8:1, and even more preferably from about 3:1 to about 5:1.

Additional Ingredients

The first or second compositions of the present invention can also comprise any additive usually used in cosmetic or dermatologic compositions. For example, waxes, film forming agents including silicone based film forming agents, organogelators, dispersants, antioxidants, a suitable carrier (oils, solvents, etc.), preserving agents, fragrances, fillers, neutralizing agents, cosmetic and dermatological active agents such as, for example, emollients, moisturizers, vitamins, hydroxy acids, essential fatty acids, UV filters, and sunscreens, surfactants and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook*.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Specific examples of additional ingredients include oils or other organic solvents, particularly if the composition is an anhydrous composition or an emulsion. Any oils or solvents can be used in accordance with the present invention. The oils or solvents can be volatile or non-volatile, silicone-based and/or hydrocarbon-based, etc. Thus, for example, the composition may contain, independently or in combination, volatile silicone oils, non-volatile silicone oils, volatile non-silicone oils, non-volatile non-silicone oils, volatile organic solvents and non-volatile organic solvents.

Preferably, oils or solvents, when present, represent from 5% to 98.4% of the total weight of the composition, more preferably from 10% to 80% of the total weight of the composition, and most preferably from 20% to 75%, including all ranges and subranges therebetween.

According to preferred embodiments, the composition may contain one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

According to other preferred embodiments, the composition may contain one or more non-silicone volatile oils and may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the entire contents of which is hereby incorporated by reference.

According to other preferred embodiments, the compositions may contain organic solvents. Representative examples of such organic solvents include physiologically acceptable solvents typically found in dermatological or cosmetic compositions such as, for example, ethanol, propanol, isopropanol, etc.

In other embodiments, the compositions of the present invention are substantially free of silicone oils (i.e., contain less than about 1% of silicone oil). In another embodiment, the compositions are substantially free of non-silicone oils (i.e., contain less than about 1% of non-silicone oil). In another embodiment, the compositions are substantially free of non-volatile oils (i.e., contain less than about 1% of non-volatile oil). In yet another embodiment, the compositions are substantially free of volatile oils (i.e., contain less than about 1% of volatile oil).

Water, when present, preferably represents from about 1% to about 70% by weight of the total weight of the composition, more preferably from about 5% to about 60% of the total weight of the composition, and most preferably from about 10% to about 50%, including all ranges and subranges therebetween. Preferably, such water-containing cosmetic compositions are emulsions or dispersions.

According to other embodiments of the present invention, the compositions are anhydrous. By "anhydrous," it is meant that the composition contains substantially no water (that is, less than about 3% by weight of the composition of water).

According to preferred embodiments of the present invention, the first composition comprising colorant and the second compositions comprising at least one polysilicone polymer and at least one silicone resin are applied to the keratin material sequentially (that is, one after the other). For example, the composition comprising the colorant can be applied to the keratin material before the composition comprising the at least one polysilicone polymer and at least one silicone resin.

According to such preferred embodiments, methods of applying colorant to a keratin material (such as, for example, skin, hair, nails, eyelashes, eyelids, eyebrows, lips) comprising applying to the keratin material a basecoat composition comprising colorant, and then applying to the basecoat composition a topcoat composition comprising at least one polysilicone polymer and at least one silicone resin are provided.

According to particularly preferred embodiments of the present invention, methods of artificially coloring hair, including coloring, touching up hair roots (that is, the portion of hair very close to yet above the scalp) or highlighting hair, comprising applying to hair a first composition comprising at least one colorant and a second composition comprising at least one silicone film forming resin and at least one polysilicone polymer are provided.

According to preferred embodiments, when a composition is applied to a keratin material in accordance with the present invention, the composition is applied in a way or manner which allows the silicone film forming resin and/or polysilicone polymer in the composition to form a film on the keratin material and the film thus formed fixes the colorant to the keratin material. Suitable manners of application include, for example, (1) applying the composition to a keratin material and leaving the composition on the keratin material without rinsing (for example, the composition is in the form of a "leave-in" composition for hair) and (2) applying the composition to a keratin material, leaving the composition on the keratin material for a sufficient amount of time to allow the silicone film forming resin and/or polysilicone polymer to form a film (for example, at least 1 minute, preferably at least 2 minutes), and then washing or shampooing the keratin material. By "fixing the colorant to the keratin material," it is meant that the film thus formed inhibits the artificial colorant from migrating away from the keratin material (for example, being washed away during rinsing or shampooing, transferring upon contact or physical disturbance such as brushing, etc.). Thus, for example, artificial colorants which attach to the keratin material remain on the keratin material owing to the formed film.

In accordance with the preceding preferred embodiments, the compositions of the present invention are applied topically to the desired area of the keratin material in an amount sufficient to preserve the artificial color which has been applied to the keratin material. The compositions may be applied to the desired area as needed.

The present invention also envisages kits and/or prepackaged materials suitable for consumer use containing one or more compositions according to the description herein (for example, kits containing (1) a composition for application to keratin material such as hair dye, mascara, eyeliner, a lip composition such as a lipstick or liquid lip color, foundation, etc.; and (2) a composition comprising at least one polysilicone polymer and at least one silicone resin. According to particularly preferred embodiments, kits comprising (a) a hair dye composition; and (b) a topcoat composition comprising at least one polysilicone polymer and at least one silicone resin are provided. Such kits may also include other compositions or components such as, for example, a cosmetic removing composition, instructions for applying or using the compositions in the kit, cosmetic application devices (for example, a mascara brush), etc.

The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis

EXAMPLE 1

Comparative Example

The following compositions were prepared.

|  | Invention Composition | Comparative Composition A | Comparative Composition B |
|---|---|---|---|
| trimethylsiloxysilicate | 20 | 0 | 20 |
| nylon 611 dimethicone copolymer | 5 | 5 | 0 |
| dimethicone | 2 | 2 | 2 |
| isododecane | 73 | 93 | 78 |

These compositions were compared via the following protocols.

Swatches of 90% Grey Hair were artificially colored using a semi-permanent composition containing a mixtures of dyes. Next, Invention Composition, Comparative Composition A and Comparative Composition B were applied to swatches. After approximately 2 minutes, the swatches were wetted, shampooed, rinsed and dried. This wetting, shampooing, rinsing and drying process continued for five cycles.

The color on each of the hair samples was then determined using the CIELAB L*a*b* system using a Minolta 2600-d calorimeter. Six measurements were taken on each swatch, three on each side of the swatch, at the top, middle and bottom of each side.

Specifically, ΔE, a measurement of color change, was calculated for each of the compositions (between treatment and standard) according to the following formula:

$$\Delta E = ((L^*_1 - L^*_0)^2 + (a^*_1 - a^*_0)^2 + (b^*_1 - b^*_0)^2)^{1/2}$$

where $L^*_0$, $a^*_0$, and $b^*_0$ are coordinates associated with a standard (artificially colored hair which was not shampooed/washed) and $L^*_1$, $a^*_a$, and $b^*_1$ are coordinates of hair to which Compositions A, B or C had been applied and shampooed 5 times.

The following results were obtained.

|  | Sample | ΔE |
|---|---|---|
| Standard | invention composition 5 | 0.67 |
| Standard | B5 | 4.03 |
| Standard | C5 | 2.46 |

From the table above, a lower ΔE value indicates better color retention or less fading of the artificial hair color. Thus, a significant difference in color retention existed between Invention Composition and the other compositions, showing that significantly better color retention or significantly less color fading was achieved using the invention composition.

What is claimed is:

1. A method for preserving artificial color on a keratin material, comprising:
applying to an artificially-colored keratin material a composition comprising siloxysilicate resin and at least one nylon 611/dimethicone copolymer;

wherein:
the siloxysilicate resin and the at least one nylon 611/dimethicone copolymer are present in a weight ratio of from about 3:1 to about 5:1; and
the siloxysilicate resin and/or the at least one nylon 611/dimethicone copolymer forms a film on the keratin material and the film fixes the artificial colorant to keratin material.

2. The method of claim 1, wherein the keratin material is hair.

3. The method of claim 1, wherein the siloxysilicate resin is present in the composition in an amount ranging from about 1% to about 50% by weight relative to the total weight of the composition.

4. The method of claim 2, wherein the siloxysilicate resin is present in the composition in an amount ranging from about 1% to about 50% by weight relative to the total weight of the composition.

5. The method of claim 1, wherein the at least one nylon 611/dimethicone copolymer is present in the composition in an amount ranging from about 1% to about 20% by weight relative to the total weight of the composition.

6. The method of claim 2, wherein the at least one nylon 611/dimethicone copolymer is present in the composition in an amount ranging from about 1% to about 20% by weight relative to the total weight of the composition.

7. The method of claim 1, wherein the composition is anhydrous.

8. The method of claim 1, wherein the siloxysilicate comprises trimethylsiloxysilicate.

\* \* \* \* \*